United States Patent [19]

Yensen

[11] Patent Number: 4,767,889

[45] Date of Patent: Aug. 30, 1988

[54] YENSEN 2A
[75] Inventor: Nicholas P. Yensen, Tucson, Ariz.
[73] Assignee: Salt Weeds, Tucson, Ariz.
[21] Appl. No.: 912,225
[22] Filed: Sep. 29, 1986
[51] Int. Cl.$^4$ .............................................. A01H 1/02
[52] U.S. Cl. ...................................................... 800/1
[58] Field of Search ............................. Plt./89; 800/1

Primary Examiner—Robert E. Bagwill
Attorney, Agent, or Firm—Cahill, Sutton & Thomas

[57] ABSTRACT

A grain variety, Yensen 2a, of *Distichlis palmeri*, which are characterized by vigorous growth in salty soils, high grain yield and ideal form for harvest. This grain variety has excellent taste qualities.

3 Claims, No Drawings

YENSEN 2A

BACKGROUND OF THE INVENTION

The present invention relates to a new and distinct variety of a grain of the family Poaceae and more particularly to a plant of the species *Distichlis palmeri* (Vasey) Fassett ex I. M. Johnston, commonly known as salt grass.

SUMMARY OF THE INVENTION

The new variety has a number of characteristics and desirable features distinguishing it as an improved variety. These characteristics are principally: a pleasing coloration of light brown which tends to be lighter posteriorly and darker anteriorly, high fertility and ideal grain from suitable for harvest, including reduced shatter characteristics.

DRAWING

The invention is illustrated in my copending application, Ser. No. 901,316.

This new variety was discovered at test plots of Salt Weeds (an Arizona partnership) in Tucson, Ariz.

DESCRIPTION OF THE PREFERRED EMBODIMENT

The new variety was noted in test plantings wherein approximately 100,000 seeds, seedlings and cuttings had been test planted under agricultural conditions on a total of 2.5 acres following over ten (10) years of study of salt-tolerant plants. The purpose of these large plants was specifically to discover new grain and plant varieties with commercial potential and to learn their agronomic requirements. The new variety, Yensen 2a, was derived from a plant produced from a bed seedling.

The new plant which first produced the new grain variety was first noted for its vigorous growth and ideal form and later for its high yield of grain on relatively short stalks. The stalks are erect and the grain heads are of a suitable height for combine harvest.

Plants which yield the new grain variety, Yensen 2a, are being reproduced via rhizomes in Tucson, Ariz., where a number of other plant and grain varieties are also being observed.

The following is a detailed description of the new variety:

PARENTAGE: A grain variety by plant variety Yensen 2a, a plant variety of *Distichlis palmeri*. The harvested caryopses from which the Yensen 1a variety emerged were among literally millions of harvested caryopses which were then selected for size and weight. While approximately 100,000 caryopses have been so selected and test planted, the particular test planting from which Yensen 1a emerged had approximately 3,000 caryopses. This test planting was in plot number 2 . . . of 9 test plots planted at Tucson, Ariz. These test plots were subjected to various stresses, e.g. water, temperature, salts, etc. such that only 0.1% to 1% of the caryopses reached maturity. The plants that survive this rigorous selection process are often phenotypically similar. This may be true in part due to similar genetic combinations that can survive the same rigorous selection process, and in part to the harvested caryopses being frequently derived from a few phenotypically similar parents. Due to (1) the nature of the selection process wherein massive numbers of caryopses are utilized, and (2) the heavy selection pressures, it is not practical to follow individual caryopses and their lineages.

GRAIN: 6-11 mm in length (including the bifurcation style), length decreasing slightly apically on the spikelet, 1-2 mm in width, 1-2 mm in height; embryo cover 2-4 mm in length; ventral surface indented with a longitudinal groove (except in unusually well-filled caryopses); anterior seed coat longitudinally wrinkled and posterior portion wrinkled into two rounded ventral keels and one rounded dorsal keel which extends to the bifurcation of the styles; surface texture with numerous longitudinal striae and light vertical rugae, glabrous, colored a brown and may be darker anteriorly and lighter posteriorly.

PROPAGATION: To date all grain described herein. It is expected that at least 90% of the grain progeny of the Yensen 2a grain will be phenotypically similar to the characteristics of the initial grain variety as they are described herein. It is acknowledged that the new grain variety is undoubtedly genetically heterozygous at a number of loci and no claim is made herewith for genetic homozygosity.

PLANT DESCRIPTION (PARENT STOCK):

Culms: Rigid, erect, occasionally branched, glabrous, 20-50 cm high depending on rhizome age at inflorescence, 2-3 mm in diameter. The color of the culms is not significantly different from some other varieties.

Rhizomes: Thick and scaled at nodes.

Blades: Firm, rigid, ascending, pointed and pungent, involute (especially upon drying), distichous, glabrous to slightly puberulent, 3-5 mm basal width, 20-30 veins at base, typically 30-80 mm in length.

Sheath: Glabrous to slightly puberulent, with a tuft of wooly hairs at either side of the mouth, ligule smooth with pubescence apically.

Inflorescence:
Panicle—erect, compoundly branched (often branched in two's), 4-8 cm in length and does not extend beyond the leaves;
Spikelet—with 5-9 flowers, subtending "bracts" infertile, 20-40 mm in length, 6-10 mm in width;
Florets—lemma 10-15 mm in length decreasing slightly apically on the spikelet, 4-6 feint veins on either side of a weak keel;
palea 9-11 mm in length, length decreasing slightly apically on the spikelet.

I claim:

1. A new and distinct grain variety, Yensen 2a, a variety of *Distichlis palmeri*, which is principally characterized by a pleasing coloration of the grain that may grade from light brown posteriorly to dark brown anteriorly, reduced shatter characteristics, high grain fertilization rate, and a grain form suitable for harvest.

2. A new and distinct grain variety, Yensen 2a, a variety of *Distichlis palmeri* which is principally distinguished by a length of 6-11 mm (including the bifurcation style), length decreasing slightly apically on the spikelet, a width of 1-2 mm, a height of 1-2 mm; embryo cover 2-4 mm in length, ventral surface indented with a longitudinal groove (except in unusually well-filled caryopses), anterior seed coat longitudinally wrinkled and posterior portion wrinkled into two rounded ventral keels and one rounded dorsal keel which extends to the bifurcation of the styles, surface texture with numerous longitudinal striae and light vertical rugae, glabrous, colored a coriaceous brown.

3. Plant material of plant variety of claim 1 selected from the group consisting of bran, endosperm, germ, or any parts thereof of combination of parts thereof.

* * * * *